United States Patent [19]

Bott et al.

[11] Patent Number: 4,996,324

[45] Date of Patent: Feb. 26, 1991

[54] PREPARATION OF ALKANOLS WHICH ARE SUBSTITUTED IN THE 1 POSITION BY AROMATIC OR HETEROCYCLIC RADICALS

[75] Inventors: Kaspar Bott, Wachenheim; Herwig Hoffmann, Frankenthal; Walter Scheidmeir, Limburgerhof; Horst Trapp, Plankstadt, all of Fed. Rep. of Germany

[73] Assignee: BASF Aktiengesellschaft, Ludwigshafen, Fed. Rep. of Germany

[21] Appl. No.: 266,270

[22] Filed: Oct. 26, 1988

Related U.S. Application Data

[63] Continuation of Ser. No. 937,822, Dec. 4, 1986, abandoned.

[30] Foreign Application Priority Data

Dec. 24, 1985 [DE] Fed. Rep. of Germany ....... 3546016

[51] Int. Cl.$^5$ .................... C07D 213/28; C07C 33/22; C07C 33/34
[52] U.S. Cl. .................................. 546/339; 546/152; 568/715
[58] Field of Search ......................... 546/339; 568/715

[56] References Cited

PUBLICATIONS

The Merck Index, Ninth Edition, p. ONR-39, published by Merck and Co., Inc. (1976).
Angew. Chem. 64 (1952), pp. 213–220.
Bulletin Soc. Chem. France, 1983, II. pp. 252–256.
Tetrahedron, 23 (1967) pp. 1723–1733.

*Primary Examiner*—Alan L. Rotman
*Attorney, Agent, or Firm*—John H. Shurtleff

[57] ABSTRACT

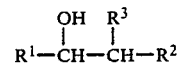

where $R^1$ is an aromatic or heterocyclic radical, $R^2$ is a straight-chain or branched alkyl raical and $R^3$ is hydrogen, methyl or ethyl, are prepared by reacting a secondary alcohol of the formula

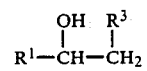

with a primary alcohol of the formula $R^2OH$ (III) in the presence of an alkali metal hydroxide at from 150° to 300° C.

15 Claims, No Drawings

PREPARATION OF ALKANOLS WHICH ARE SUBSTITUTED IN THE 1 POSITION BY AROMATIC OR HETEROCYCLIC RADICALS

This application is a continuation, of application Ser. No. 937,822 filed Dec. 4, 1986, abandoned.

The present invention relates to a process for the preparation of alkanols, which are substituted in the 1 position by aromatic or heterocyclic radicals, by reacting a secondary alcohol with a primary alcohol.

It is known that isoalcohols having a higher molecular weight can be obtained from aliphatic alcohols by autocondensation in the presence of an alkali metal hydroxide at elevated temperatures. This reaction, named after Guerbet (cf. Angew. Chem. 64 (1952), 213–220), takes place in accordance with the following equation:

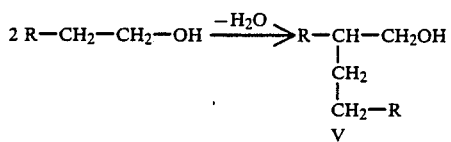

where R is alkyl.

In this way, it is possible, for example, to obtain 2-ethylhexanol ($R=C_2H_5$) from n-butanol in high yields if the water formed during the condensation is distilled off from the reaction mixture. The good selectivity of such a Guerbet synthesis is achieved in particular because the mixed condensation of the branched alcohol of the formula V with the starting material of the formula IV is not very favored.

Subsequently, it was found that it is also possible, on the basis of this reaction principle, to carry out crossed Guerbet syntheses with high selectivity if, in addition to the alkanol, methanol (Bull. Soc. Chim. France 1983, II, pages 252–256) or benzyl alcohol (Tetrahedron, 23 (1967), 1723–1733) is used as a further reactant. In the last-mentioned case, the hydroxyl group of the benzyl alcohol appears in the water of reaction, while the OH radical of the alkanol is found in the condensate:

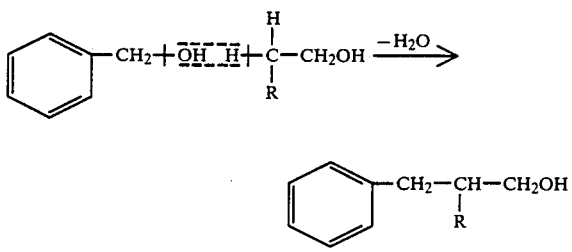

We have found, surprisingly, that alkanols of the formula

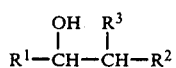

where $R^1$ is an aromatic or heterocyclic radical, $R^2$ is a straight-chain or branched alkyl radical of 1 to 20 carbon atoms and $R^3$ is hydrogen, methyl or ethyl, are obtained if a secondary alcohol of the formula

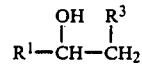

is reacted with a primary alcohol of the formula $R^2OH$ (III) where $R^1$, $R^2$ and $R^3$ have the above meanings, in the presence of an alkali metal hydroxide at from 150° to 300° C.

The novel process makes it possible for the alkanols which are substituted in the 1 position by aromatic or heterocyclic radicals to be prepared in a particularly economical manner. Surprisingly, the hydroxyl group in the starting materials of the formula II does not participate in the chemical reaction. It was also not to be expected that it would be possible for alkanols having branched carbon chains to be used so successfully as alkanols of the formula III, and that, for example where alkanols of the formula IV are used, there would be virtually no autocondensation of these alkanols to form the compounds of the formula V.

In the secondary alcohols of the formula II, $R^1$ is an aromatic radical, such as phenyl, which may furthermore contain substituents such as alkyl of 1 to 4 carbon atoms or phenyl, or $R^1$ is a heterocyclic radical, such as pyridyl or quinolyl. Specific examples of alcohols of the formula II are 1-phenylethanol, 1-phenylpropanol, 1-phenylbutanol, 1-(pyrid-3-yl)-ethanol, 1-(pyrid-3-yl)-propanol, 1-(pyrid-3-yl)-butanol, 1-(quinol-2-yl)-ethanol, 1-(quinol-3-yl)-ethanol and 1-(quinol-3-yl)-propanol.

The primary alcohols of the formula III are straight-chain or branched alkanols where alkyl is of 1 to 20, preferably 1 to 15, carbon atoms. Specific examples are n-propanol, n-butanol, 2-ethylhexanol, and the isononanols and isodecanols which are readily obtainable by hydroformylation of dimeric butene and trimeric propylene, respectively.

The secondary alcohols of the formula II are reacted with the primary alcohols of the formula III in the presence of an alkali metal hydroxide, such as potassium hydroxide or sodium hydroxide, at from 150° to 340° C., preferably from 200° to 300° C., in particular from 200° to 270° C. The molar ratio of alcohol component II to alcohol component III in the mixture may vary within wide limits, for example from 1:5 to 5:1. Preferably, the starting materials are used in an equimolar ratio. The alkali metal hydroxide is employed in amounts of from 0.5 to 5, preferably from 0.5 to 3, in particular from 0.5 to 1.5, % by weight, based on the mixture of the two alcohols. In order to achieve very high conversion of the reactants II and III, it is advantageous if the water formed is distilled off with one of the starting materials.

The usefulness of the novel process is increased by virtue of the fact that the alcohols obtainable in this manner can be converted to the corresponding hydrocarbons by catalytic hydrogenation, and linear or branched carbon chains of defined structure can thus be introduced into an aromatic ring. Furthermore, by dehydrogenation of the secondary OH group, the products can be converted to the corresponding acylophenones, which are usually prepared in a more complicated manner by reacting a carbonyl chloride with an aromatic hydrocarbon using an equimolar amount of aluminum chloride.

EXAMPLES 1 TO 4

Equimolar amounts of the alcohols of the formula II and III stated in the table as starting materials were reacted together with 1% by weight, based on the alcohol mixture, of potassium hydroxide for 10 hours at 270° C. in a stirred autoclave having a capacity of 0.3 L.

The water of reaction was not separated off during the reaction. From the gas chromatographic analyses of the reacted mixtures, both the conversion and the selectivity of the formation of the alkanols of the formula I were calculated by setting the percentages by area equal to the percentages by weight for all the components in the gas chromatogram.

The formulae of the resulting alkanols, the conversion and the selectivity are shown in the table.

TABLE

| Example No. | Starting materials II | Starting materials III | Structural formula of the resulting alcohol of the formula I | Selectivity, based on converted alcohol II | Conversion, based on alcohol II |
|---|---|---|---|---|---|
| 1 | Ph–CH(OH)–CH$_3$ | n-C$_4$H$_9$–OH | Ph–CH(OH)–n-C$_5$H$_{11}$ | 86% | 64% |
| 2 | Ph–CH(OH)–CH$_3$ | CH$_3$–(CH$_2$)$_3$–CH(C$_2$H$_5$)–CH$_2$OH | Ph–CH(OH)–(CH$_2$)$_2$–CH(C$_2$H$_5$)–(CH$_2$)$_3$–CH$_3$ | 90% | 62% |
| 3 | Ph–CH(OH)–CH$_3$ | iso-C$_9$H$_{19}$–OH | Ph–CH(OH)–CH$_2$–iso-C$_9$H$_{19}$ | 95% | 62% |
| 4 | Ph–CH(OH)–C$_2$H$_5$ | CH$_3$OH | Ph–CH(OH)–CH(CH$_3$)$_2$ | 98% | 34% |

We claim:

1. A process for the preparation of an alkanol of the formula $$R^1-\underset{\underset{\text{OH}}{|}}{CH}-\underset{\underset{R^3}{|}}{CH}-R^2 \quad \text{I}$$

where R$^1$ is a member selected from the group consisting of phenyl, pyridyl and phenyl substituted by alkyl of 1 to 4 carbon atoms; R$^2$ is a straight-chain or branched alkyl of 1 to 15 carbon atoms and R$^3$ is hydrogen, methyl or ethyl, which process comprises:

reacting a secondary alcohol of the formula $$R^1-\underset{\underset{\text{OH}}{|}}{CH}-\underset{\underset{R^3}{|}}{CH_2} \quad \text{II}$$

with a primary alcohol of the formula R$^2$OH (III) where R$^1$, R$^2$ and R$^3$ have the above meanings, in the presence of an alkali metal hydroxide at from 150° to 300° C.

2. A process as claimed in claim 1, wherein potassium hydroxide is used as the alkali metal hydroxide.

3. A process as claimed in claim 1, wherein the reaction is carried out at from 200° to 300° C.

4. A process as claimed in claim 1, wherein the secondary alcohol of the formula II contains, as the aromatic radical R$^1$, phenyl which may furthermore contain alkyl groups of 1 to 4 carbon atoms.

5. A process as claimed in claim 1, wherein the secondary alcohol of the formula II contains pyridyl as the heterocyclic radical R$^1$.

6. A process as claimed in claim 1, wherein the molar ratio of the starting material II to starting material III in the mixture is from 1:5 to 5:1.

7. A process as claimed in claim 1, wherein the alkali metal hydroxide is used in an amount of from 0.5 to 5% by weight, based on the mixture of the two alcohols.

8. A process as claimed in claim 1, wherein R$^2$ of the primary alcohol III is alkyl of 1 to 10 carbon atoms.

9. A process as claimed in claim 1, wherein the alcohol II is selected from the group consisting of 1-phenylethanol, 1-phenylpropanol, 1-phenylbutanol, 1-(pyrid-3-yl)-ethanol, 1-(pyrid-3-yl)-propanol, 1-(pyrid-3-yl)-butanol, and the primary alcohol III is selected from the group consisting of n-propanol, n-butanol, 2-ethylhexanol, isononanols and isodecanols.

10. A process as claimed in claim 1, wherein the alcohol II is 1-phenylethanol and the alcohol III is selected from the group consisting of n-butanol, 2-ethylhexanol and isononanol.

11. A process as claimed in claim 1, wherein the alcohol II is 1-phenylpropanol and the alcohol III is methanol.

12. A process as claimed in claim 1 wherein R$^2$ as alkyl contains from 8 to 10 carbon atoms.

13. A process as claimed in claim 1 wherein R$^1$ is phenyl.

14. A process as claimed in claim 1 wherein R$^1$ is pyridyl.

15. A process as claimed in claim 1 wherein R$^1$ is phenyl substituted by alkyl of 1 to 4 carbon atoms.

UNITED STATES PATENT AND TRADEMARK OFFICE
CERTIFICATE OF CORRECTION

PATENT NO. : 4,996,324

DATED : February 26, 1991

INVENTOR(S) : Kaspar Bott, Herwig Hoffmann, Walter Scheidmeir and Horst Trapp

It is certified that error appears in the above-identified patent and that said Letters Patent is hereby corrected as shown below:

After "ABSTRACT", the first line before the formula should read --Alkanols of the formula--.

Signed and Sealed this

Eighteenth Day of August, 1992

Attest:

DOUGLAS B. COMER

Attesting Officer

Acting Commissioner of Patents and Trademarks